(12) United States Patent  
Bhola et al.

(10) Patent No.: US 10,752,873 B2  
(45) Date of Patent: Aug. 25, 2020

(54) MULTI-ANALYTE SENSING USING HYDROGELS AND MAGNETOMETERS

(71) Applicant: APPLIED BIOSENSORS LLC, Salt Lake City, UT (US)

(72) Inventors: Vishal Bhola, Salt Lake City, UT (US); Prashant Tathireddy, Salt Lake City, UT (US)

(73) Assignee: Applied Biosensors, LLC, Salt Lake City, UT (US)

( * ) Notice: Subject to any disclaimer, the term of this patent is extended or adjusted under 35 U.S.C. 154(b) by 618 days.

(21) Appl. No.: 15/006,172

(22) Filed: Jan. 26, 2016

(65) Prior Publication Data

US 2016/0215253 A1 Jul. 28, 2016

Related U.S. Application Data

(60) Provisional application No. 62/107,978, filed on Jan. 26, 2015.

(51) Int. Cl.
| | | |
|---|---|---|
| C12M 1/36 | (2006.01) | |
| C12M 1/00 | (2006.01) | |
| C12M 1/34 | (2006.01) | |

(52) U.S. Cl.
CPC ............ *C12M 41/48* (2013.01); *C12M 23/28* (2013.01); *C12M 41/00* (2013.01); *C12M 41/32* (2013.01)

(58) Field of Classification Search
CPC ...... C12M 41/00; C12M 41/32; C12M 41/48; C12M 23/28
See application file for complete search history.

(56) References Cited

U.S. PATENT DOCUMENTS

2012/0170050 A1 7/2012 Savran et al.

FOREIGN PATENT DOCUMENTS

WO WO 2009146147 A2 12/2009

OTHER PUBLICATIONS

Mönch, Ingolf, et al. "Rolled-up magnetic sensor: nanomembrane architecture for in-flow detection of magnetic objects." ACS nano 5.9 (2011): 7436-7442.*
Song, S. H., et al. "A wireless chemical sensor featuring iron oxide nanoparticle-embedded hydrogels." Sensors and Actuators B: Chemical 193 (2014): 925-930.*
Sridhar, Vijayalakshmi, and Kenichi Takahata. "A hydrogel-based passive wireless sensor using a flex-circuit inductive transducer." Sensors and Actuators A: Physical 155.1 (2009): 58-65.*
Horton, B., et al. "A Wireless, Passive pH Sensor Based on Magnetic Higher-Order Harmonic Fields." Journal of Medical Devices 3.2 (2009): 027548.*

(Continued)

*Primary Examiner* — Robert J Eom
(74) *Attorney, Agent, or Firm* — Thorpe North & Western, LLP

(57) ABSTRACT

A sensor, especially for a reactor, bioreactor, or a clinical or animal research application, is disclosed including a sensor probe having at least one sensor unit associated therewith, each sensor unit including a hydrogel, a magnetic sheet disposed on one side of the hydrogel, and a magnetometer disposed on a side of the hydrogel opposite the magnetic sheet.

16 Claims, 11 Drawing Sheets
(4 of 11 Drawing Sheet(s) Filed in Color)

(56) References Cited

OTHER PUBLICATIONS

Ruan, Chuanmin, Kefeng Zeng, and Craig A. Grimes. "A mass-sensitive pH sensor based on a stimuli-responsive polymer." Analytica Chimica Acta 497.1-2 (2003): 123-131.*

Hison, Cornelia, et al. "A magnetoelastic amorphous ribbon in a silicone sheath as stress sensor and self indicator of strain threshold." Sensors and Actuators A: Physical 106.1-3 (2003): 164-167.*

Horton, Brock E., et al. "A Wireless, Passive pH Sensor Based on Magnetic Higher-Order Harmonic Fields." Sensor Letters 7.4 (2009): 599-604. (Year: 2009).*

Bai et al.; "A Double-Imprinted Diffraction-Grating Sensor Based on a Virus-Responsive Super-Aptamer Hydrogel Derived from an Impure Extract"; Angewandte Chemie International Edition; (2014); pp. 2095-2098; vol. 53; <doi: 10.1002/anie.201309462 >.

Bai et al.; "Macromolecular Amplification of Binding Response in Superaptamer Hydrogels"; Journal of the American Chemical Society; (Apr. 18, 2013); pp. 6977-6984; vol. 135, No. 18; <doi: 10.1021/ja400576p >.

Gong et al.; "Development of the Double Cyclic Peptide Ligand for Antibody Purification and Protein Detection"; Bioconjugate Chemistry; (Jun. 30, 2016); pp. 1569-1573; vol. 27, Issue 7; <doi: 10.1021/acs.bioconjchem.6b00170 >.

Roque et al.; "An artificial protein L for the purification of immunoglobulins and Fab fragments by affinity chromatography"; Journal of Chromatography A; (Feb. 4, 2005); pp. 157-167; vol. 1064, Issue 2; <doi: 10.1016/j.chroma.2004.11.102 >.

Roque et al.; "Synthesis and screening of a rationally designed combinatorial library of affinity ligands mimicking protein L from *Peptostreptococcus magnus*"; Journal of Molecular Recognition; (2005); pp. 213-224; vol. 18, Issue 3; <doi: 10.1002.jmr.733 >.

Yang et al.; "Engineering Target-Responsive Hydrogels Based on Aptamer-Target Interactions"; Journal of American Chemical Society; (2008); pp. 6320-6321; vol. 130, Issue 20; <doi: 10.1021/ja801339w >.

* cited by examiner

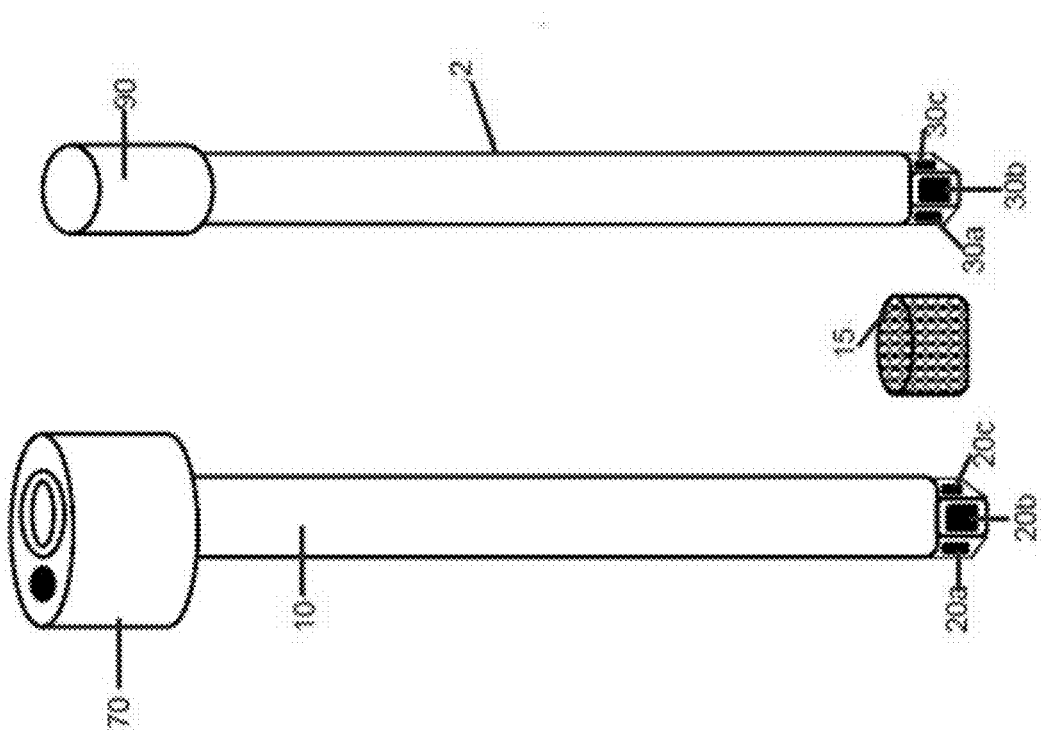

MULTI-ANALYTE SENSING USING HYDROGELS AND MAGNETOMETERS

CROSS REFERENCE TO RELATED APPLICATIONS

The application claims the benefit of U.S. Application No. 62/107,978 filed Jan. 26, 2015, the entire disclosure of which is incorporated herein by reference.

REFERENCE TO GOVERNMENT GRANTS

Portions of the disclosure herein may have been supported in part by grants from the National Science Foundation Grant No STTR IIP 1321572 (Phase 1 subcontract through Applied Biosensors). The United States Government may have certain rights in this application.

FIELD OF THE INVENTION

The disclosed invention relates to sensors useful, inter alia, for biomedical applications, including but not limited to clinical and animal research applications; bio-process control in biotech manufacturing facilities, cell culture research, and waste water treatment applications; and other applications employing sensors.

BACKGROUND OF THE INVENTION

In general, single-use bioreactors are a cheaper alternative to traditional glass/steel bioreactors. Moreover, single-use bioreactors come in wide range of size and form factors, allowing for easier storage and configurability as compared to steel/glass reactors. There is an increasing demand for single-use technologies in the bioprocess industry. However, there are limited and expensive choices for single-use sensors to fit into the bioreactors. Thus, a need exists for single-use sensors for reactors in general, including bioreactors. The invention is directed to these, as well as other, important ends.

SUMMARY OF THE INVENTION

Accordingly, the present invention relates to single-use or disposable sensors that can monitor the concentration of different analytes in an environment, such as a reactor, particularly a bioreactor, and thus help in efficient control of the process parameters. The sensor unit may be integrated with the reactor set-up, where a single sensor unit houses multiple smart polymers to allow continuous monitoring of multiple analytes, replacing the need for multiple sensors, each monitoring different analytes. The present design is compatible both with conventional steel/glass reactors, where it can be inserted in the standard size port, and with the single-use polymeric vessels, where the unit can be inserted into a standard port pre-welded to the reactor.

In one embodiment, the invention provides a sensor for an environment, such as biomedical applications (particularly clinical and animal research applications) and reactors, particularly bioreactors, including a sensor probe having at least one sensor unit associated therewith, each sensor unit including a hydrogel, a magnetic sheet disposed on one side of the hydrogel, and a magnetometer disposed on a side of the hydrogel opposite the magnetic sheet.

In another embodiment, the invention provides a system for process control in a vessel, such as a bioprocess vessel. The system includes a multi-part sensor assembly design capable of being inserted into a port of the bioprocess vessel, wherein the assembly includes one or more smart polymers each having a tailored chemistry for recognition of an analyte, a sheath to hold the one or more smart polymers on the outside thereof, and an electronics module to transduce, process, and transmit the signals from the smart polymers; and a controller configured for signal processing and deconvolution of data obtained from each of the one or more smart polymers.

Other aspects of the invention will become apparent by consideration of the detailed description and accompanying drawings. The accompanying drawings, which are included to provide a further understanding of the invention and are incorporated in and constitute a part of this specification, illustrate embodiments of the invention and together with the description serve to explain the principles of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fees.

FIG. 9 shows disposable sensor sheath and reusable electronic insert portions from the exemplary shake-flask sensor design of FIG. 8.

DETAILED DESCRIPTION OF THE INVENTION

Figure 1A:
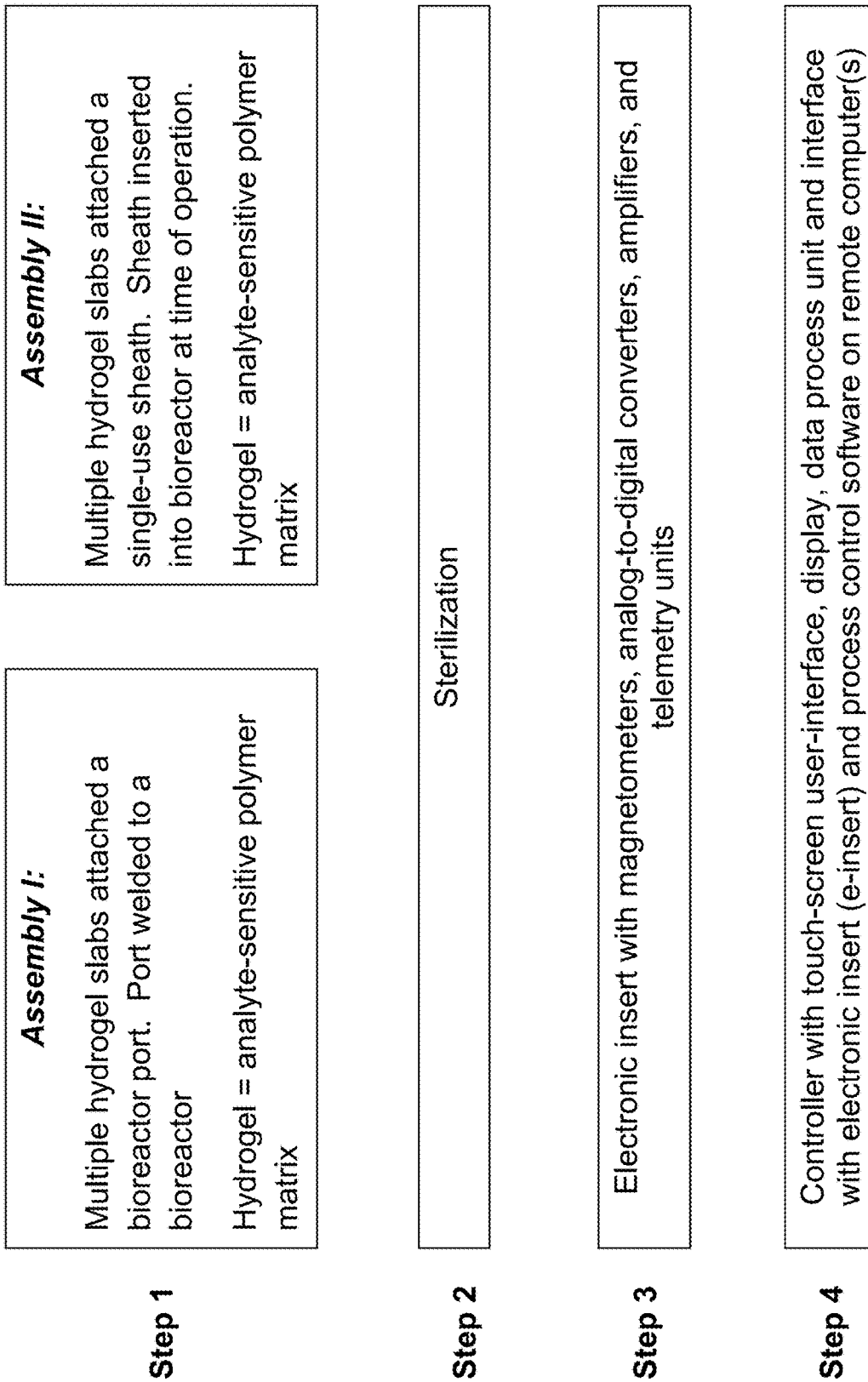
FIG. 1A shows the exemplary method of preparing the sensor assembly design components.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Definitions

The following definitions are provided for the full understanding of terms used in this specification.

As used herein, the article "a" means "at least one," unless the context in which the article is used clearly indicates otherwise.

As used herein, a "smart polymer" includes a polymer that responds to changes in environmental parameters, analyte concentration, temperature, pH and the like.

As used herein, a "sheath" refers to a plastic casing (which may be single-use) to which the smart polymers are attached on the outside of the casing.

As used herein, an "electronics insert" or "e-insert" includes electronics for operation of the magnetometers and telemetry. The magnetometers on the e-insert are aligned to smart polymers on the sheath during sensor operation.

As used herein, a "sensor" includes an assembly comprising the sheath, the e-insert, and other related components, such as mesh (e.g. to protect the smart polymers).

As used herein, a "magnetometer" includes a magnetoresistive sensor (AMR/GMR) that measures the magnetic field variation as a change in the resistance, where AMR means "Aniso Magnetoresistive" and GMR means "Giant Magnetoresistive." A magnetometer can also be any combination of components capable of measuring changes in magnetic field, such as inductive coils, etc.

Reference will now be made in detail to the preferred embodiments of the invention, examples of which are illustrated in the drawings and the examples. This invention may, however, be embodied in many different forms and should not be construed as limited to the embodiments set forth herein. In addition and as will be appreciated by one of skill in the art, the invention may be embodied as a product, method, system or process.

Accordingly, in one aspect, the invention is directed to a sensor design for use, inter alia, in biomedical applications (particularly clinical and animal research applications) and in reactors, particularly bioreactors, including both single-use polymeric vessels as well as conventional non-disposable reactors, especially bioreactors. The sensor design is realized as a multi-part assembly, and is described below.

In various exemplary embodiments, sensor assembly design components include and as prepared generally described in FIG. 1A:

Smart polymers may be used for sensing the changes in different analyte concentrations over time, including, for example, smart hydrogels with tailored chemistry to make them responsive to a particular analyte concentration. The hydrogels in a preferred embodiment include a magnetic sheet on the top (where "top" refers to a side of the hydrogel facing away from the magnetometer), such that the swelling/deswelling of the hydrogels can be transformed to changes in magnetic field variation. In various embodiments the magnetic sheet is made of niobium. In other embodiments, the magnetic sheet is made of a plurality of magnetic particles arranged in an approximately planar configuration, for example within a hydrogel or other polymer. In certain embodiments, the magnetic field of the magnetic sheet is oriented in a uniform direction; in other embodiments, the magnetic field of the magnetic sheet has a particular arrangement such as a Halbach array.

In certain embodiments, a sheath holds the smart polymers, for example, a glass, polymer, or non-magnetic sheath, to hold the hydrogels in the preferred embodiment. The polymers and magnetic materials are arranged in such a way that there is no significant effect of one magnetic material on a magnetometer from a neighboring sensor unit, or the arrangement of polymers and magnetic materials is configured to allow easy post-processing of any effects of the neighboring magnetic materials. The smart polymers may be physically or chemically attached to the sheath.

Transducers convert the changes in physical attributes of the smart polymers to a form measurable electronically. For example, the transducers may include magnetometers to convert the changes in magnetic field upon swelling/deswelling of the hydrogels to changes in the magnetometer resistance values or inductance values.

Offset magnetic sheets to shift the magnetometer range and sensitivity in the region of interest. For example, addition of an offset magnet offsets the hydrogel-associated magnet's magnetic field such that the effective magnetic field observed by the magnetometer is shifted. This enables a stronger magnetization of the hydrogels' magnetic sheet and hence a higher slope for the magnetic field, which also translates to a higher sensitivity in the sensor setup.

Electronics to transmit or/and process the signal from the transducers to a controller/display for continuous monitoring of the transmitted data. For example, when using magnetoresistive magnetometers, the electronics convert the changes in the resistance to appropriate changes in the voltage/current which can then be processed to represent the changes in hydrogel swelling/deswelling and then to the change in analyte concentration. The mode of data transmission can be wired (e.g. USB interface) or wireless (e.g. Bluetooth, ZigBee® or Wi-Fi). The latter wireless option would require a transmitting unit at the sensor end and a receiver at the processing end, which would be one of the controllers for the reactor or the computer, for further processing of the data and subsequent use in controlling the reactor parameters. In certain embodiments, a remote computer receives data from the electronics module. The remote computer may include a controller that decouples the data from each of the one or more smart polymers using algorithms, such as but not limited to Artificial Neural Networks, K-means clustering, and Principal Components Analysis.

A mesh enclosure, particularly a plastic mesh enclosure, for the smart polymers protects them from any damage during handling and to reduce the turbulence close to the smart polymers.

Thus in some embodiments the sensor may be used in a reactor, particularly a bioreactor. The sensor may include a sensor probe having at least one sensor unit associated therewith. Each sensor unit may include a hydrogel, a magnetic sheet disposed on one side of the hydrogel, and a magnetometer disposed on a side of the hydrogel opposite the magnetic sheet. The sensor probe may include a sheath surrounding an electronics insert, wherein the hydrogel of each sensor unit is attached to the sheath and the magnetometer of each sensor unit is attached to the electronics insert. The electronics unit may be removably disposed within the sheath, i.e., inserted into the sheath, such that each magnetometer aligns with a respective hydrogel.

The sensor may also include a plurality of sensor units associated with the sensor probe, where each sensor unit may have a hydrogel that is sensitive to a different analyte.

The sensor probe may have various shapes including an elongated rod. As described herein, the plurality of sensor units in some embodiments may be disposed at an end of the elongated rod around an outer perimeter of the rod. In other embodiments, the plurality of sensor units may be disposed along a length of the elongated rod. In yet other embodiments, the plurality of sensor units may be disposed at an end of the elongated rod.

Each sensor unit may include an offset magnet disposed on a side of the magnetometer opposite the hydrogel. The offset magnet generally has a magnetic field strength that is lower than a magnetic field strength of the magnetic sheet, for example the magnetic field strength of the offset magnet may be between 0.5× and 0.9× the magnetic field strength of the magnetic sheet. In certain embodiments a magnetic field direction of the offset magnet has an orientation that is opposite a magnetic field direction of the magnetic sheet.

In use, the sensor may be used to implement a method of measuring an analyte concentration in an environment, such as a reactor, bioreactor, or a clinical or animal research application. The method may include one or more of the steps of: exposing the hydrogel to a sample containing an unknown amount of an analyte that is recognized by the hydrogel, such that interaction of the analyte with the hydrogel causes swelling or deswelling of the hydrogel and movement of the magnetic sheet relative to the magnetometer; monitoring a magnetic resistance value of the magnetometer; and converting the magnetic resistance value to an analyte level.

The single-use components listed above may be made to be sterilizable and hence compatible with most of the process control environments. Furthermore, there are different ways of assembling these components:

Exemplary Assembly I

The hydrogels are placed on the part to the standard port that is welded to the reactor during the manufacturing of single-use reactors. The e-insert is a separate insert which goes inside the above-mentioned part in a way that facilitates alignment of the electronics with the hydrogels. The e-insert is used at the time of operation.

Exemplary Assembly II

The hydrogels are arranged on a plastic sheath and the sheath is inserted into a port at the time of operation along with the e-insert.

Examples of Sensor Configuration in Exemplary Assembly II

The three proposed configurations are presented in FIGS. 1B to 1D, as described below where:

1 Sensor
2 Electronic insert (e-insert) assembly
3 Sheath assembly
10 Sheath (e.g., plastic)
20 Hydrogel (specific hydrogels 20a, 20b, 20c, 20d, 20e, 20f)
30 Magnetometer (specific magnetometers 30a, 30b, 30c, 30d, 30e, 30f)
40 PCB for magnetometer
50 Magnetic sheet (50a, 50b, 50c, 50d, 50e)

Figures 1B, 1C, 1D:
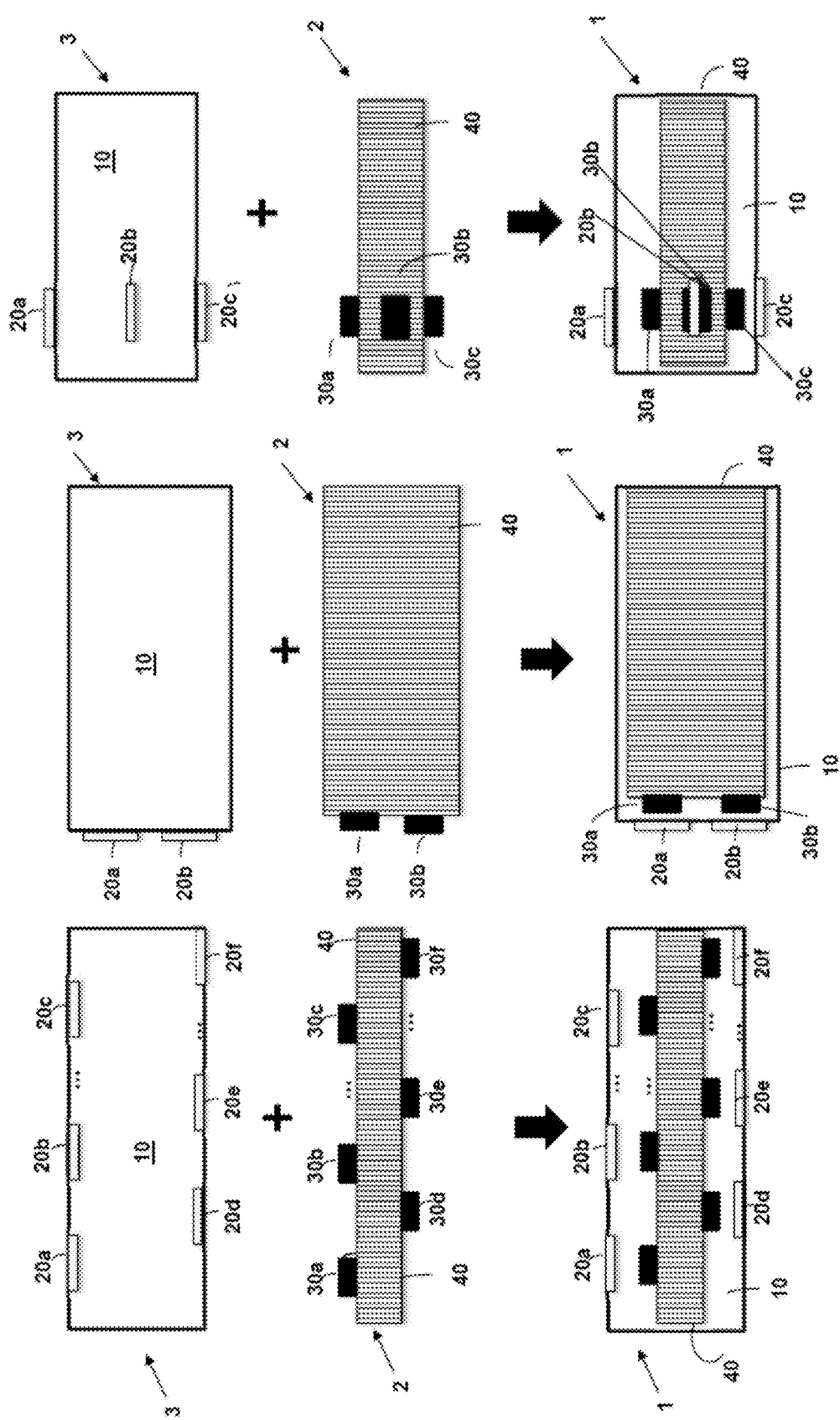
FIGS. 1B to 1D show three representative example configurations for the hydrogel sheath and electronics insert.

Exemplary Configuration I (FIG. 1D)

Figure 2A:
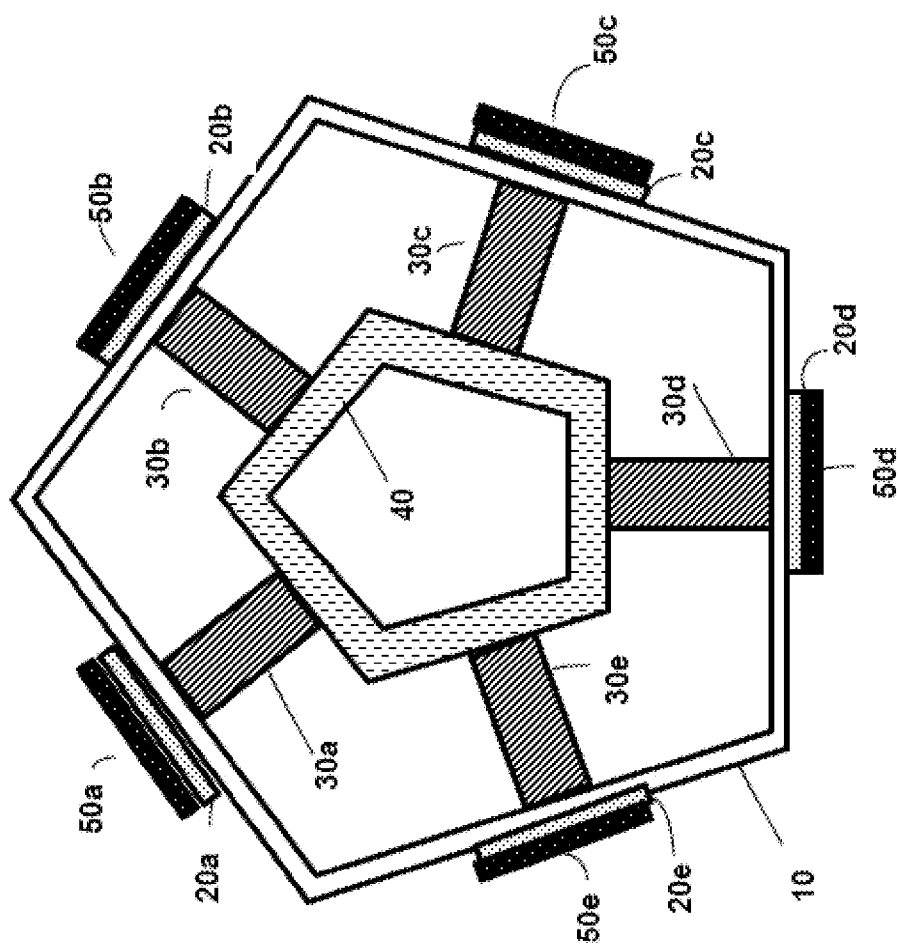
FIG. 2A shows the top view and FIG. 2B shows the side view of the three-dimensional geometry design for the five smart polymers in configuration I. The hydrogel sensors, each with a magnetic sheet on top, are arranged in a symmetric pentagonal sheath. The magnetometers on the PCB are part of the electronics-insert aligned with the center of the hydrogels.
Figure 2B:
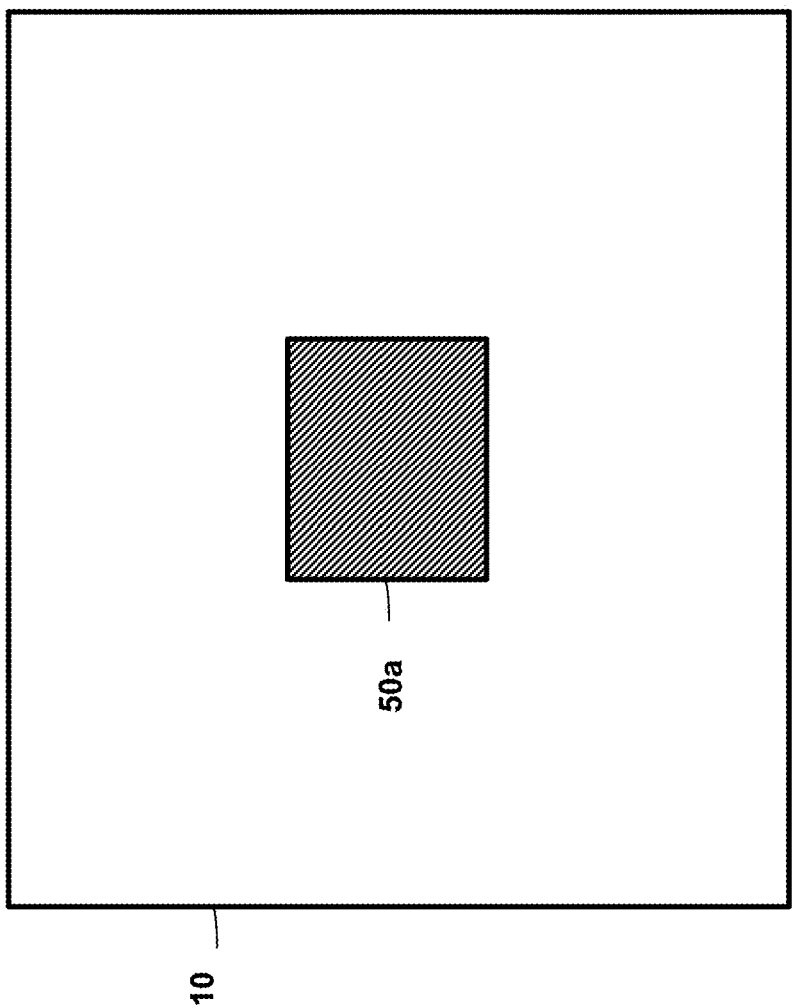

The smart hydrogels (20a, 20b, 20c, 20d, 20e, 20f) are arranged in a symmetric fashion on the sheath. FIG. 2A shows the hydrogels with magnetic sheets (50a, 50b, 50c, 50d, 50e) on top, arranged in a symmetric pentagonal geometry. FIG. 2B shows the side view for magnetic sheet 50a. Smart hydrogel 20a (not shown) is located behind magnetic sheet 50a. The smart polymers may be physically or chemically attached to the sheath.

Each of these smart hydrogels, are designed to respond when the concentration of a particular analyte changes inside the reactor solution, or a clinical or animal research application. The response typically is in the form of hydrogel swelling/deswelling, which in turn leads to a change in the distance of the magnetic source from the magnetometer and hence a change in the magnetic field recorded by the magnetometer.

Figure 3:
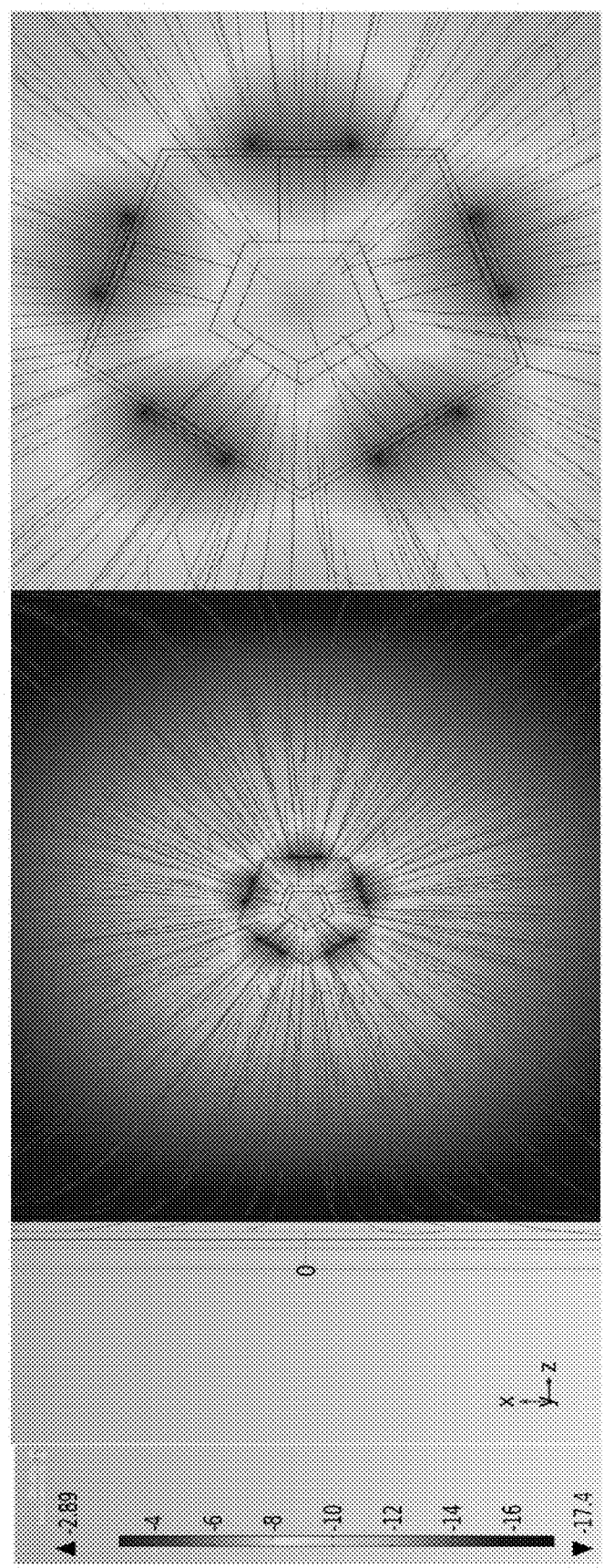
FIG. 3 shows that the repulsion between field lines cause nearly zero magnetic field at the geometry center.

Placing the hydrogel in a geometry as shown in FIG. 2A has both advantages and limitations. Because the hydrogels (20a, 20b, 20c, 20d, 20e) are placed in a close vicinity to each other and all of the magnetic sheets (50a, 50b, 50c, 50d, 50e) are magnetized in the inward direction, the field lines repel each other to the point that there is negligible magnetic field at the center of the geometry. An example of this effect is shown in FIG. 3. The repulsion creates a natural dip in the magnetic field strength observed by the magnetometers as compared to the field strength for a single isolated magnetic sheet. This in turn allows a larger magnetization on the magnetic sheets and/or closer distance to the magnetometers. Closer distance implies a higher slope of the magnetic field which translates to higher sensitivity.

Figure 4:
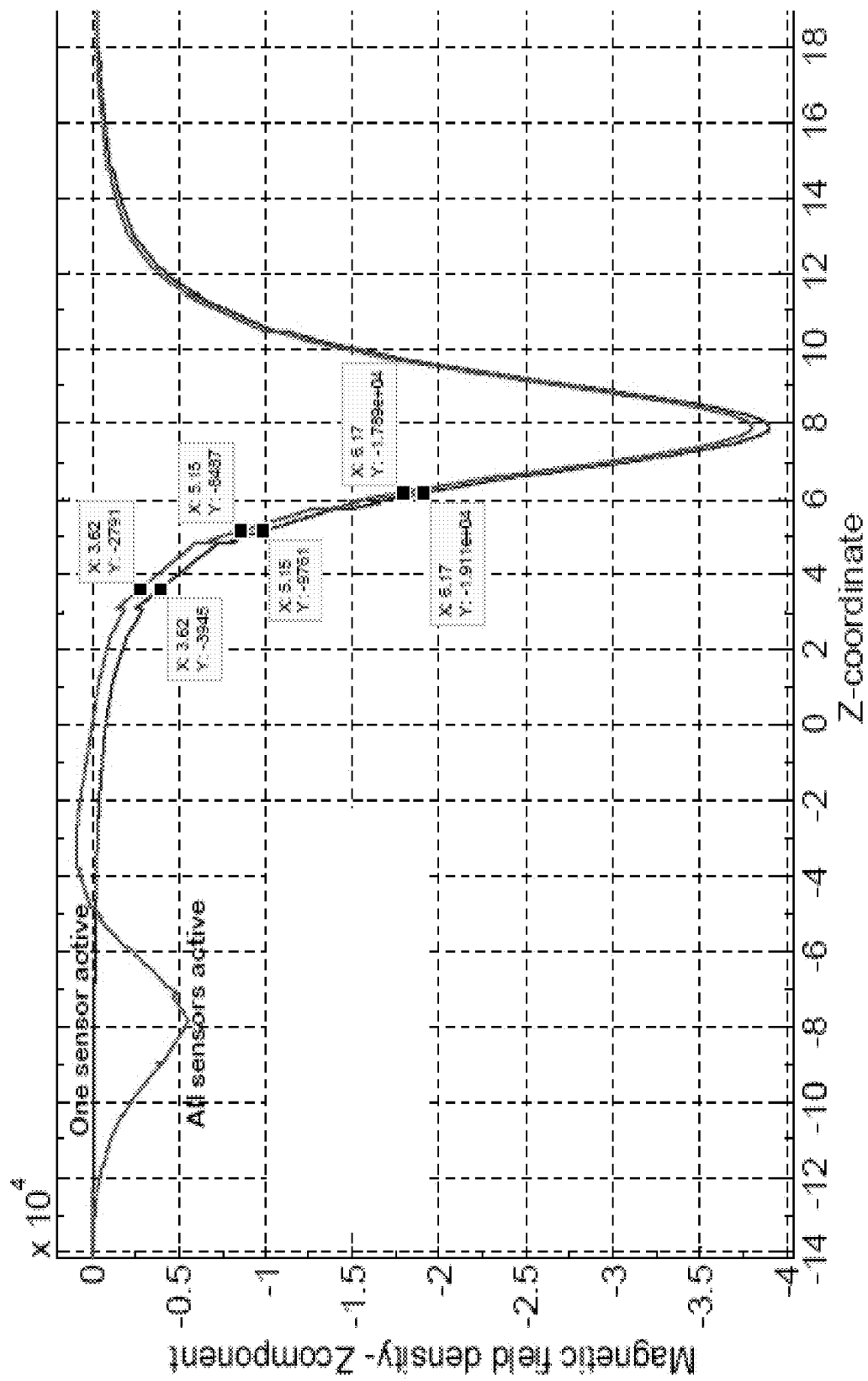
FIG. 4 shows that the magnetic field (Z-component) variation with distance for an isolated magnetic sheet follows a nearly cubic relation as expected. The introduction of all the magnetic sheets causes a dip in the field strength, with nearly the same slope. The boxes highlight the dip in the magnetic field at various points.

However, in the event of concentration change of multiple analytes within the reactor, or a clinical or animal research application, there is bound to be some effect of the magnetic field variation due to swelling/deswelling of one hydrogel on the field observed by rest of the four magnetometers. This effect is shown in FIG. 4. For this, one of the five hydrogels can be used as a reference to eliminate the ambient noise in the signal from the other magnetometers when the hydrogels are placed inside the reactor for continuous analyte monitoring.

The dip in magnetic field values as well as maximum change in magnetic field on a selected hydrogel-magnetometer due to swelling/deswelling of the rest is shown in TABLE 1.

TABLE 1

| SheetM (kA/m) | Offset (in mG) | ΔB1 (in mG) | ΔB4 (in mG) |
|---|---|---|---|
| 10 | 660 | 38 | 6 |
| 20 | 1320 | 76 | 12 |
| 30 | 1980 | 113 | 18 |
| 40 | 2640 | 151 | 24 |
| 50 | 3300 | 189 | 30 |
| 60 | 3960 | 227 | 36 |

TABLE 1 shows the offset (dip in the magnetic field strength) and the change in magnetic field upon 10% swelling of the hydrogel(s).

Exemplary Configuration II (FIG. 1C)

The hydrogels (20a, 20b) can all be placed at bottom of the sheath 10, such that the all of them are on the outside of the sheath and electronics (30a, 30b align from the inside.

Exemplary Configuration III (FIG. 1B)

Alternatively, the hydrogels (20a, 20b, 20c, 20d, 20e) can all be placed at relatively further distances from one another (including, e.g., in an alternating/offset pattern), such that the magnetic field variation of one hydrogel has negligible effect on the others. This makes the processing relatively easier but increases the sensor size in order to accommodate the larger distances between the hydrogels.

Improving the Sensor Performance

The magnetometers offer limited magnetic field range and resolution. For example, a HMC1052Z magnetometer offers the maximum detectable magnetic field range as ±6 Gauss for a supply voltage of 3V to the IC. Therefore, even though the magnetic sheets at magnetization≥30 kA/m offer high slope regions ~10 mGauss/µm at the magnetometer, the use of these magnetic sheets is inhibited by the fact that the absolute magnetic field strength (>6 Gauss) is beyond the magnetometer's working range. For magnetization strengths<30 kA/m, the magnetic field strength is within the magnetometer's range. However, the slope falls to about 5 mG/µm, which theoretically is higher than the magnetometer's resolution but fails experimentally to resolve 1 µm movement steps of the magnetic source.

Figure 5:
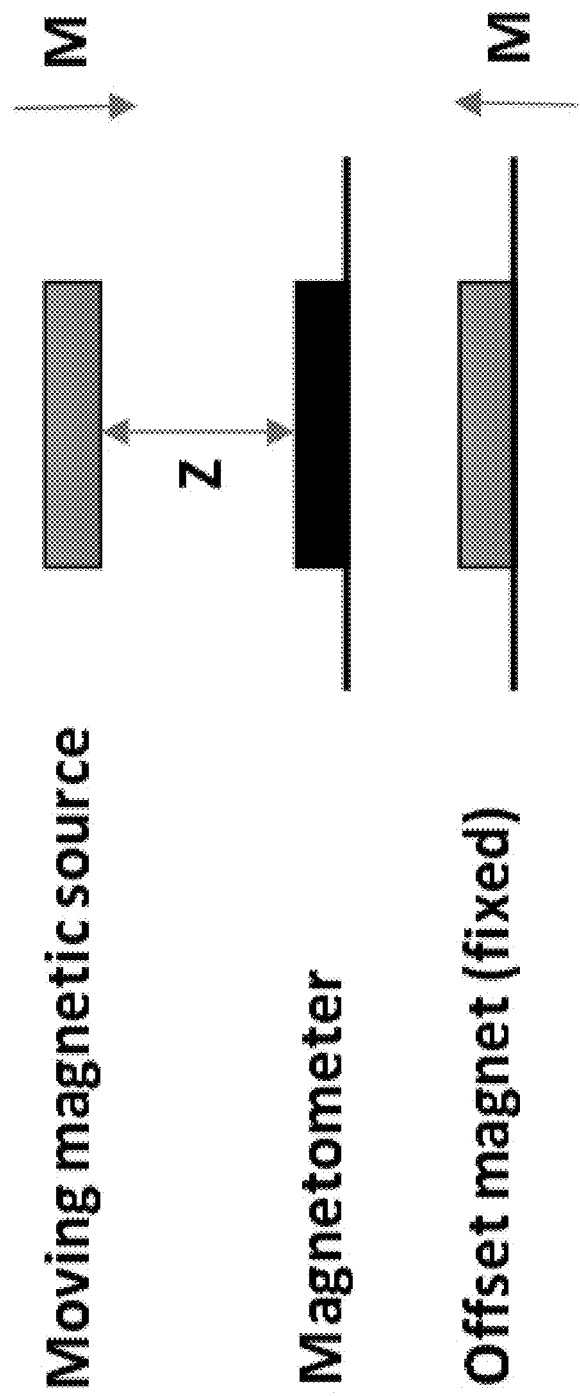
FIG. 5 shows a conceptual diagram for the offset magnet application. The offset magnet is fixed with respect to the magnetometer (which may also be fixed) and shifts the magnetic field of the moving magnet source.

The present invention overcomes this problem by the addition of offset magnets as shown in FIG. 5. This creates a shift in the magnetic field and allows the moving magnet to be closer to the magnetometer and hence have higher slope (sensitivity). The effect is visible from the plot in FIG. 6, where the sensitivity nearly doubles upon addition of a single magnetic sheet.

The offset magnet feature can be extended to the present multianalyte hydrogel configurations, where there is an offset magnet for each of the hydrogel's magnetic sheets. The latter acts as the movable component, which moves upon the swelling/deswelling of the hydrogel.

Figure 6:
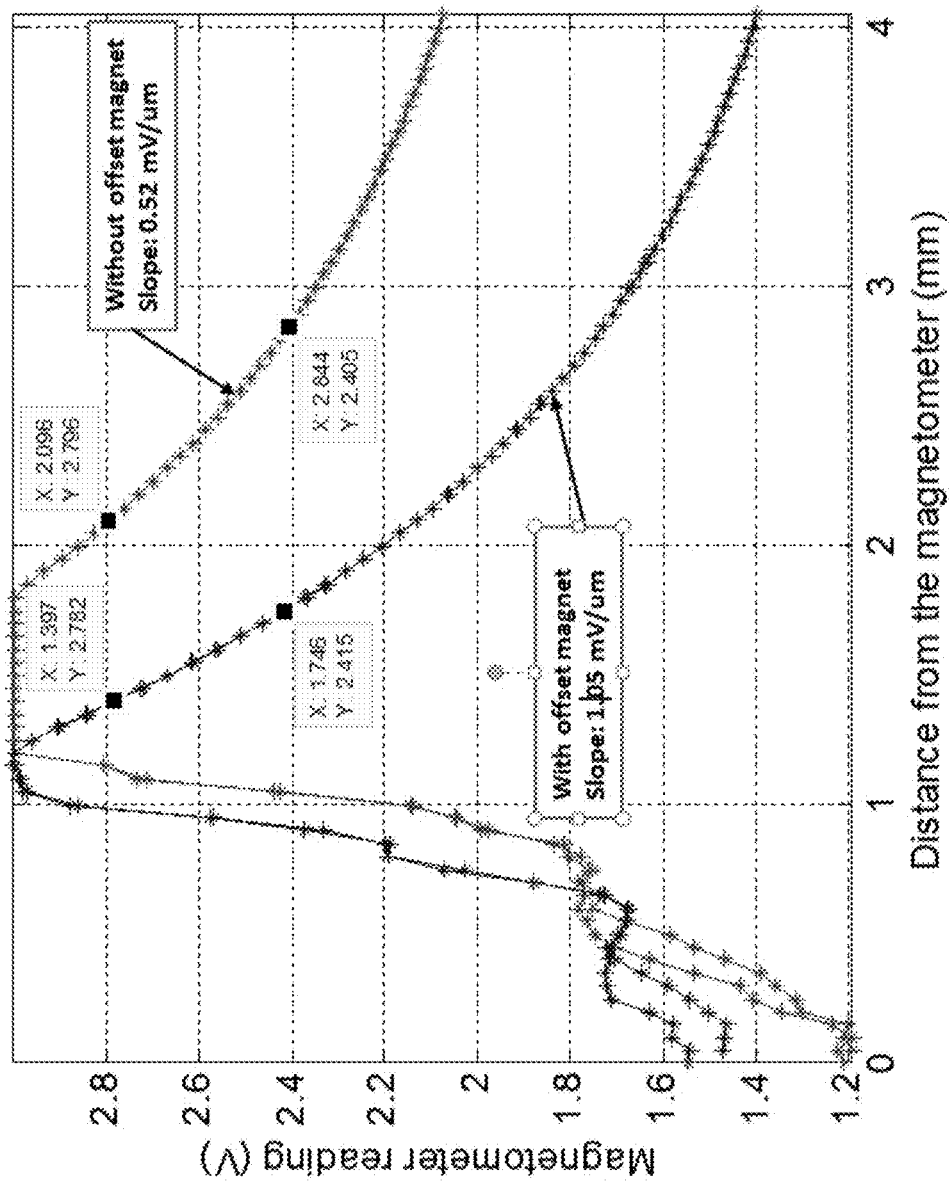
FIG. 6 shows results for an experiment conducted with ("slope: 1.05") and without ("slope: 0.52") the offset magnet. The application of an offset magnet not only extends the useable range, it also nearly doubles the sensitivity from 0.52 mV/µm to 1.05 mV/µm.

After adding offset magnets, configuration II would be similar to FIG. 5, because the hydrogels are at considerably larger distances, such that they can be treated individually. A 2× gain in sensitivity is expected for each of the magnetometers as shown in FIG. 6. This is in accordance with the results obtained from COMSOL Multiphysics simulations.

Figure 7:
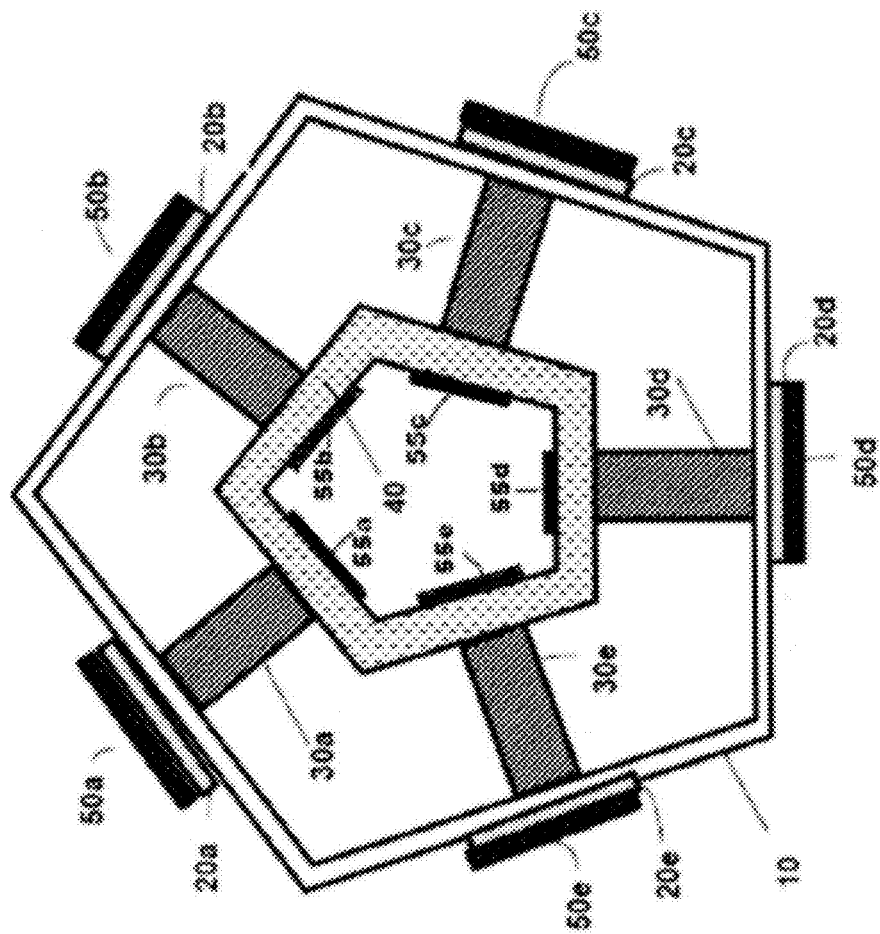
FIG. 7 shows the addition of offset magnets to the geometry design presented in FIG. 2A.

The new geometry for Configuration I with this modification is shown in FIG. 7. As earlier, the offset magnets (55a, 55b, 55c, 55d, 55e) have the same thickness as the magnetic sheets (50a, 50b, 50c, 50d, 50e) associated with hydrogel sensors (20a, 20b, 20c, 20d, 20e). However, the offset magnets are magnetized at 0.5× to 0.9× of the magnetization (magnetic field strength) of the hydrogel sensor magnetic sheets, to obtain the optimum combination which was found to be 0.8× to 0.9× in one of the embodiments. The dip in the magnetic field strength is lower as compared to the earlier case without any offset magnets. However, the sensitivity is nearly doubled in all of the cases. The dip in magnetic field values as well as maximum change in magnetic field on a selected hydrogel-magnetometer due to swelling/deswelling of the rest is shown in TABLE 2.

FIG. 7 shows addition of offset magnets (55a, 55b, 55c, 55d, 55e) to the geometry design presented in FIG. 2.

TABLE 2 shows the offset (dip in the magnetic field strength) and the change in magnetic field upon 10% swelling and deswelling of the hydrogel(s).

TABLE 2

| SheetM (kA/m) | Offset (in mG) | $\Delta B1_{swell}$ (in mG) | $\Delta B4_{swell}$ (in mG) | $\Delta B1_{deswell}$ (in mG) | $\Delta B4_{deswell}$ (in mG) |
|---|---|---|---|---|---|
| 40 | −1878 | 185 | 13 (7%) | 171 | 8 (4.7%) |
| 50 | −2347 | 231 | 16 (6.9%) | 214 | 10 (4.7%) |
| 60 | −2816 | 277 | 20 (7.2%) | 257 | 12 (4.7%) |

$\Delta$B1Swell: Change in magnetic field at M1 due to 10% swelling of HG1
$\Delta$B1DeSwell: Change in magnetic field at M1 due to 10% swelling of HG1
$\Delta$B4Swell: Change in magnetic field at M1 due to 10% swelling of HG2:HG5
$\Delta$B4DeSwell: Change in magnetic field at M1 due to 10% swelling of HG2:HG5

A comparison of the performance of the multianalyte sensor for the two configurations described above is shown in TABLE 3.

TABLE 3

| Slope | Magnetization (kA/m) | One sensor active | All sensors active | | Magnetization (kA/m) | One sensor active | All sensors active |
|---|---|---|---|---|---|---|---|
| Low | 10 | 1.520478 | 1.48556 | | | | |
| Low | 20 | 3.040956 | 2.971119 | | | | |
| Low | 30 | 4.561433 | 4.456679 | | | | |
| * | 40 | 6.081911 | 5.942238 | ~2× gain | 40** | 13.75626 | 11.38139 |
| * | 50 | 7.602389 | 7.427798 | ~2× gain | 50** | 17.19533 | 14.22672 |
| * | 60 | 9.122867 | 8.913357 | ~2× gain | 60** | 20.63439 | 17.07208 |

*Field strength outside magnetometer range
**Field strength within magnetometer range As can be seen from TABLE 3, a ~2× gain in the sensitivity is obtained with the addition of offset magnets. Moreover, the magnetic fields strengths are in the magnetometer's range (±6 Gauss).

Figure 8:
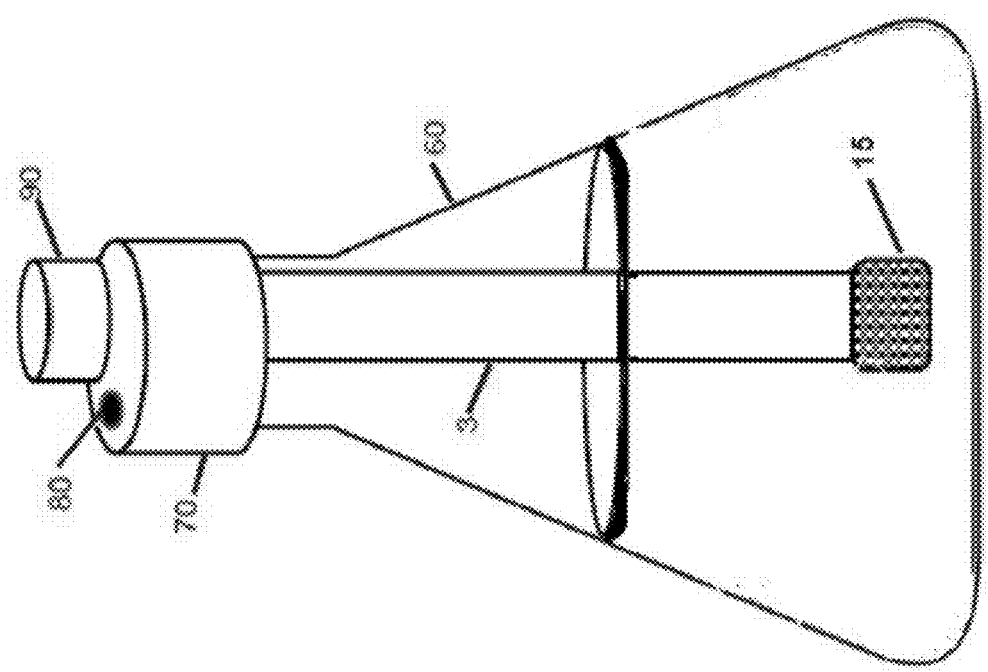
FIG. 8 shows an exemplary shake-flask sensor design.

FIG. 8 shows an exemplary shake-flask sensor design. The sensor 1 with e-insert assembly 2 (not shown) topped with the electronics housing for telemetry 90 and sheath assembly 3 capped with protective mesh 15 is inserted into flask 60 through cap 70. A port 80 permits access to the flask without disturbing the sensor 1.

FIG. 9 shows the disposable sensor sheath 10 that makes up the sheath assembly 3 and reusable electronic insert 90 used in FIG. 8. The reusable e-insert assembly 2 is topped with the electronics housing for telemetry 90 and fits within disposable sheath assembly 3 capped with protective mesh 15. Analyte-specific hydrogels 20 are attached at the end of the disposable sheath assembly 3. The magnetometers 30 are attached at the end of the reusable e-insert assembly 2 and align with the specific hydrogels 20 on the disposable sensor sheath 3.

In certain embodiments, the sensor usage and methodology may include one or more of the following:
Wi-Fi/USB/ZigBee® transmission of the data to controller/desktop computer;
Software to decouple the data coming from different hydrogels for highly selective data; and
Integration as a feedback mechanism with the controller to achieve optimized process control In certain embodiments, the multi-sensor configuration is arranged in symmetric fashion may obtain maximum sensitivity and magnetometer range. In certain other embodiments, the single sensor assembly can sense multiple analytes at the same time. In yet other embodiments, the use of offsetting magnets to enhance the magnetometers' range and sensitivity. In certain embodiments, the sensor configuration allows improved performance compared to conventional sensors without making any changes to the existing reactor designs or a clinical or animal research application. In certain embodiments, the computer program may decouple the data from the different smart polymers present in the sensor assembly and thereby eliminate ambient noise. In another embodiment, the single sensor assembly can sense multiple analytes at the same time, whereas convention sensor technology requires multiple sensors for different analytes.

In certain embodiments, the sensor system is calibrated using a one point or a two point calibration method prior to its operation following its integration with the reactor vessel. In other embodiments, data from the sensor assembly can be integrated in a closed-loop system to maintain parameters for the bioprocess vessel at optimum levels.

The present invention provides an inexpensive solution with fixed one-time cost for the electronics and lower costs for the disposable components as compared to conventional sensor technology. The sensor configuration of the invention allows improved performance compared to conventional sensors without the necessity for making any changes to the existing reactor designs. Importantly, there is no need to draw the samples out from the reactor, as is the case with most convention sensors, exposing the reactor to contamination and reducing yield. Only the hydrogel sheath and needs to be sterilized before use, e-insert does not come in contact with the reactor solution, or a clinical or animal research application. The invention provides for multi-analyte sensing in a single unit for many different applications, including, but not limited to, bioprocess control in industrial bioreactors, cell culture research, waste water treatment, and the like. The sensors of the invention may also work as long-term sensors for biomedical applications, including clinical and animal research applications.

In certain embodiments, the sensors' range and sensitivity etc. are improved in different sensing applications by using magnetic field variation is employed as the transduction method.

It will be apparent to those skilled in the art that various modifications and variations can be made in the present invention and specific examples provided herein without departing from the spirit or scope of the invention. Thus, it is intended that the present invention cover the modifications and variations of this invention that come within the scope of any claims and their equivalents.

When ranges are used herein for physical properties, such as molecular weight, or chemical properties, such as chemical formulae, all combinations, and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A sensor, comprising: a sensor probe having at least one sensor unit associated therewith, each sensor unit comprising: a hydrogel; a permanent magnetic sheet coupled to one side of the hydrogel to form a laminate structure; and a magnetometer coupled to a side of the hydrogel opposite the permanent magnetic sheet such that swelling or deswelling of the hydrogel causes movement of the permanent magnetic sheet relative to the magnetometer, wherein an entirety of the magnetometer is part of the laminate structure.

2. The sensor of claim 1, wherein the sensor probe comprises a sheath surrounding an electronics insert, wherein the hydrogel of each sensor unit is attached to the sheath and the magnetometer of each sensor unit is attached to the electronics insert.

3. The sensor of claim 2, wherein the electronics unit is removably disposed within the sheath such that each magnetometer aligns with a respective hydrogel.

4. The sensor of claim 3, wherein the sensor probe comprises a plurality of sensor units associated with the sensor probe.

5. The sensor of claim 4, wherein the sensor probe comprises an elongated rod.

6. The sensor of claim 5, wherein the plurality of sensor units are disposed at an end of the elongated rod around an outer perimeter of the rod.

7. The sensor of claim 5, wherein the plurality of sensor units are disposed along a length of the elongated rod.

8. The sensor of claim 5, wherein the plurality of sensor units are disposed at an end of the elongated rod.

9. The sensor of claim 1, wherein each sensor unit further comprises an offset magnet disposed on a side of the magnetometer opposite the hydrogel and the offset magnet is fixed with respect to the magnetometer, both the offset magnet and the magnetometer oriented on the side of the hydrogel opposite the permanent magnetic sheet, such that the offset magnet shifts the magnetometer range and sensitivity.

10. The sensor of claim 9, wherein the offset magnet has a magnetic field strength that is lower than a magnetic field strength of the permanent magnetic sheet.

11. The sensor of claim 10, wherein the magnetic field strength of the offset magnet is between about 0.5x and about 0.9x the magnetic field strength of the permanent magnetic sheet.

12. The sensor of claim 9, wherein a magnetic field direction of the offset magnet has an orientation that is opposite a magnetic field direction of the permanent magnetic sheet.

13. The sensor of claim 1, wherein each sensor unit comprises a hydrogel that is sensitive to a different analyte.

14. The sensor of claim 1, wherein the permanent magnetic sheet and the magnetometer are not electrically conductively coupled.

15. A reactor comprising: a vessel having a port attached thereto; and the sensor of claim 1 inserted into the port.

16. A method of measuring an analyte concentration, comprising: exposing the sensor of claim 1 to a sample containing an unknown amount of an analyte that is recognized by the hydrogel in the sensor, such that interaction of the analyte with the hydrogel causes swelling or deswelling of the hydrogel and movement of the permanent magnetic sheet relative to the magnetometer; monitoring a magnetic resistance value of the magnetometer; and converting the magnetic resistance value to an analyte level.

* * * * *